(12) United States Patent
Wojciechowski et al.

(10) Patent No.: US 11,701,041 B2
(45) Date of Patent: Jul. 18, 2023

(54) ROBOTIC INTERACTIONS FOR OBSERVABLE SIGNS OF INTENT

(71) Applicant: AEOLUS ROBOTICS, INC., South San Francisco, CA (US)

(72) Inventors: Sławomir Wojciechowski, Wrocław (PL); Gregg Podnar, Lakewood, OH (US); T. William Mather, Philadelphia, PA (US); Theodore Enns, Menlo Park, CA (US); Daniel Oblinger, San Francisco, CA (US)

(73) Assignee: AEOLUS ROBOTICS, INC., San Jose, CA (US)

( * ) Notice: Subject to any disclaimer, the term of this patent is extended or adjusted under 35 U.S.C. 154(b) by 902 days.

(21) Appl. No.: 16/421,126

(22) Filed: May 23, 2019

(65) Prior Publication Data

US 2019/0358820 A1 Nov. 28, 2019

Related U.S. Application Data

(60) Provisional application No. 62/675,729, filed on May 23, 2018, provisional application No. 62/675,730, filed on May 23, 2018.

(51) Int. Cl.
*A61B 5/16* (2006.01)
*B25J 11/00* (2006.01)
(Continued)

(52) U.S. Cl.
CPC ............ *A61B 5/165* (2013.01); *A61B 5/0077* (2013.01); *A61B 5/1113* (2013.01);
(Continued)

(58) Field of Classification Search
CPC ..... B25J 11/009; B25J 11/0005; B25J 11/008; B25J 9/0003; B25J 9/163; B25J 9/1661;
(Continued)

(56) References Cited

U.S. PATENT DOCUMENTS 9,582,080 B1 * 2/2017 Tilton ...................... G06F 3/015
9,814,425 B2 * 11/2017 Tran ...................... A61B 5/7225
(Continued)

FOREIGN PATENT DOCUMENTS

JP 2002-230555 A 8/2002
JP 2003-225228 A 8/2003
(Continued)

OTHER PUBLICATIONS

PCT International Search Report and Written Opinion, PCT Application No. PCT/US201933842, dated Aug. 15, 2019, 12 pages.
(Continued)

*Primary Examiner* — Khoi H Tran
*Assistant Examiner* — Nhi Q Bui
(74) *Attorney, Agent, or Firm* — Fenwick & West LLP (57) ABSTRACT

Described herein are assistant robots that anticipate needs of one or more people (or animals). The assistant robots may recognize a current activity, knowledge of the person's routines, and contextual information. As such, the assistant robots can provide or offer to provide appropriate robotic assistance. The assistant robots can learn users' habits or be provided with knowledge regarding humans in its environment. The assistant robots develop a schedule and contextual understanding of the persons' behavior and needs. The assistant robots may interact, understand, and communicate with people before, during, or after providing assistance. The robot can combine gesture, clothing, emotional aspect, time, pose recognition, action recognition, and other observational data to understand people's medical condition, current activity, and future intended activities and intents.

20 Claims, 6 Drawing Sheets

(51) Int. Cl.
- *A61B 5/00* (2006.01)
- *B25J 9/16* (2006.01)
- *G16H 50/20* (2018.01)
- *B25J 9/00* (2006.01)
- *G10L 15/22* (2006.01)
- *G06V 20/00* (2022.01)
- *G06V 40/20* (2022.01)
- *G16H 50/30* (2018.01)
- *A61B 5/11* (2006.01)
- *G06V 10/80* (2022.01)
- *G06V 20/10* (2022.01)

(52) U.S. Cl.
CPC .......... *A61B 5/1128* (2013.01); *A61B 5/4803* (2013.01); *A61B 5/7267* (2013.01); *A61B 5/746* (2013.01); *B25J 9/0003* (2013.01); *B25J 9/163* (2013.01); *B25J 9/1661* (2013.01); *B25J 9/1697* (2013.01); *B25J 11/0005* (2013.01); *B25J 11/008* (2013.01); *B25J 11/009* (2013.01); *G06V 10/811* (2022.01); *G06V 20/10* (2022.01); *G06V 20/35* (2022.01); *G06V 40/20* (2022.01); *G06V 40/28* (2022.01); *G10L 15/22* (2013.01); *G16H 50/20* (2018.01); *G16H 50/30* (2018.01); *A61B 2560/0242* (2013.01); *A61B 2560/0252* (2013.01); *A61B 2560/0257* (2013.01); *A61B 2560/0261* (2013.01); *A61B 2562/0247* (2013.01); *A61B 2562/0271* (2013.01); *G10L 2015/223* (2013.01); *G10L 2015/228* (2013.01)

(58) Field of Classification Search
CPC ....... B25J 9/1697; G16H 50/20; G06N 20/00; G06V 20/35; G06V 40/28; A61B 5/0077; A61B 5/4803; A61B 5/7267; A61B 5/746; A61B 2560/0252; A61B 2560/0257; A61B 2560/0261; A61B 2562/0247; A61B 2562/0271; G10L 15/22; G10L 2015/223; G10L 2015/228
See application file for complete search history.

(56) References Cited

U.S. PATENT DOCUMENTS

| | | | |
|---|---|---|---|
| 2009/0055019 | A1 | 2/2009 | Stiehl et al. |
| 2011/0263946 | A1* | 10/2011 | el Kaliouby ............. A61B 5/16 600/300 |
| 2016/0193732 | A1* | 7/2016 | Breazeal .............. B25J 11/0005 700/258 |
| 2019/0145902 | A1* | 5/2019 | Tan ........................ H04L 67/12 702/35 |
| 2019/0184569 | A1* | 6/2019 | Huang ................. G05D 1/0088 |

FOREIGN PATENT DOCUMENTS

| | | |
|---|---|---|
| JP | 2004-337556 A | 12/2004 |
| JP | 2005-237668 A | 9/2005 |
| JP | 2010-140119 A | 6/2010 |

OTHER PUBLICATIONS

Japan Patent Office, Office Action, JP Patent Application No. 2020-565775, dated Jan. 11, 2022, eight pages.

Japanese Office Action, Japan Patent Office Application No. 2020-565775, dated Jul. 19, 2022, 11 pages.

* cited by examiner

| Action 402 | Audio 403 | Time 404 | Location 405 | Body Temperature 406 | Gas 407 | Rate 408 | Label 409 |
|---|---|---|---|---|---|---|---|
| Enter into a room | any | any | bathroom | any | any | > 15 within 24 hours | Too frequent bathroom visits |
| Open a window | any | any | any | any | any | > 15 within 24 hours | Too frequent window opening |
| any | any | any | any | <35.5 C or >37.5 C | any | any | Body temperature anomaly |
| any | any | any | any | any | Co2 | any | Dangerous gas detection |
| Walking | any | Between 1AM and 4:30 AM | any | any | any | any | Sleep walking |
| any | Coughing | any | any | any | any | > 10 times within 1 hour | Respiratory system problems |

| Action 602 | Audio 603 | Time 604 | Location 405 | Pose 606 | Gesture 607 | Label 608 |
|---|---|---|---|---|---|---|
| Point out | any | any | any | any | Point out | Wants an object |
| Take shoes | any | morning | hallway | any | any | Leaves the house |
| Make the bed | any | night | bedroom | any | any | Goes to sleep |
| Scattered clothes | any | any | any | any | any | Needs cleaning |
| Cook | any | afternoon | kitchen | any | any | Dinner cooking |

FIG. 6

ROBOTIC INTERACTIONS FOR OBSERVABLE SIGNS OF INTENT

CROSS REFERENCE TO RELATED APPLICATIONS

This application claims the benefit of U.S. Provisional Application 62/675,729, entitled "System and Method for Robotic Interactions for Observable Signs of Core Health," filed May 23, 2018, and U.S. Provisional Application 62/675,730, entitled "System and Method for Robotic Interactions for Observable Signs of Intent," filed May 23, 2018, both of which are incorporated herein by reference in their entirety.

BACKGROUND

This description generally relates to robots, and specifically to assistant robots.

Human companionship is necessary for everyone's physical and mental well being. A reliable and responsible companion that caters to one's needs, provides support, helps with house chores, interacts with people, and fulfills many other social functions is costly and difficult to find. With the drastic advancement in technology areas, home assistants have been becoming more popular. However, conventional home assistants are limited in their capabilities. For example, smart speakers are only able to answer queries and commands, and robot vacuum cleaners are only able to clean floors.

SUMMARY

Described herein are assistant robots that anticipate needs of one or more people (or animals). The assistant robots may recognize a current activity, knowledge of the person's routines, and contextual information. As such, the assistant robots can provide or offer to provide appropriate robotic assistance.

The assistant robots can learn users' habits or be provided with knowledge regarding humans in its environment. The assistant robots develop a schedule and contextual understanding of the persons' behavior and needs. The assistant robots may interact, understand, and communicate with people before, during, or after providing assistance. Examples of observational recognition can include body language, human interaction with recognized objects, routines over time, and human motions. The robot can combine gesture, clothing, emotional aspect, time, pose recognition, action recognition, and other observational data to understand people's medical condition, current activity, and future intended activities and intents.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
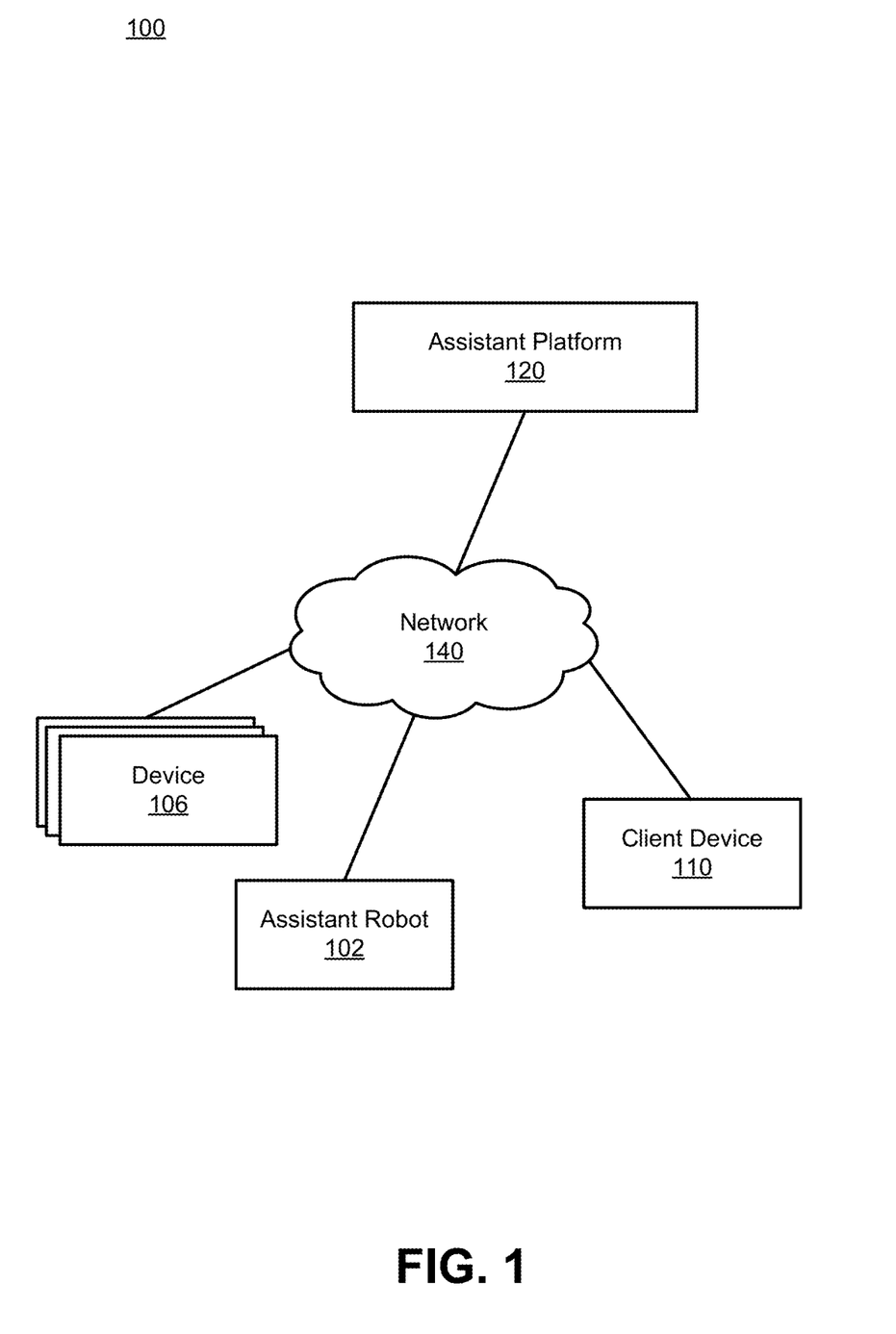
FIG. 1 is a diagram of a system environment for managing assistant robots according to one embodiment.

FIG. 1 is a diagram of a system environment for managing assistant robots according to one embodiment. The system environment includes an assistant platform 120, client device 110, assistant robot 102, devices 106, all of which are connected via a network 140. In other embodiments, different and/or additional entities can be included in the system architecture. The environment can be a residential environment, a health care environment, or a work environment.

The client device 110 is a computing device capable of receiving user input as well as transmitting and/or receiving data via the network 140. A client device is a device having computer functionality, such as a smartphone, personal digital assistant (PDA), a mobile telephone, tablet, laptop computer, desktop computer, a wearable computer (such as a smart watch, wrist band, arm band, chest band, or the like), or another suitable device. In one embodiment, a client device executes an application allowing a user of the client device 110 to interact with the assistant robot 102 and/or the assistant platform 120. For example, a client device 110 executes a browser application to enable interaction between the client device 110 and the assistant platform 120 via the network 140. An individual, via the client device 110 may control physical mobility and manipulation of the assistant robot 102. The individual may be remote from and able to control the assistant robot 102 to assist another individual. For example, a caregiver, emergency contact, or a physician may interact with the assistant robot 102 to assist a user. In another embodiment, a client device 110 interacts with the assistant platform 120 through an application programming interface (API) running on a native operating system of the client device, such as IOS® or ANDROID™.

The assistant robot 102 (further described below with reference to FIG. 2) provides assistance such as monitoring and determining a user's health, monitoring and determining the user's intent, attending to the user by performing actions based on the user's health and/or intent. The assistant robot 102 is mobile and can move around a space, e.g., a house. The assistance robot 102 can interact with people and animals. For example, the assistant robot 102 may bring an object to the user, provide information to the user, or send an alert to a contact, among many other actions. The assistant robot 102 records data about users such as the user's physical appearance, behavior, mental condition, and action, and data about the environment such as time, location, and temperature. For example, the assistant robot 102 includes various sensors to collect the data about the users and the environment. The assistant robot 102 analyzes the data to determine the user's health condition and/or the user's intent. The assistant robot 102 can move, and can interact with the user, for example, via voice, touch, etc.

The assistant platform 120 is a computer server including one or more databases storing information about the assistant robots 102, users, health information, human behavior information, and the like. The information about the assistant robots 102 may include the model, configuration, performance, etc. The information about the users may include the users' demographic information, geographic location, contact information, medical experiences, etc. The health information may include information describing illness and associated symptoms, information describing human behavior and associated medical conditions, information describing injury and associated human behaviors, information describing mental illness and physical manifestations, etc. The human behavior information may include information describing human behavior and associated tasks, information describing human behavior and associated objectives, information describing an environment and associated common human reaction in the environment, information describing a context and associated common human reaction in the context, and the like.

The devices 106 are devices that are available to the user in the environment. The environment can be a residential environment, a work environment, or a health care environment. The devices 106 can be home devices, work devices, health care devices, or transportation equipment. Example of devices include home appliances (e.g., air conditioner, heater, air venting, refrigerator, oven, coffee machine, lighting, door locks, power blinds and shades, standing desk, recliner chair, stair lift, music player, television, home theater, audio players, bathroom appliances, vacuum), office equipment (e.g., printer, copier, scanner), transportation equipment (e.g., scooter, bike, automobile, wheel chair), health care monitoring devices (e.g., blood pressure monitor, glucose meter, heart rate monitor, etc.) The devices 106 can include other types of devices that are not listed here. The devices 106 may include interfaces such that the assistant robot 102 or remote users may interact with the devices 106.

The network 140 provides a communication infrastructure between the assistant robots 102, the client devices 110, the devices 106, and the assistant platform 120. The network 140 may be any network, including but not limited to a Local Area Network (LAN), the Internet, a Metropolitan Area Network (MAN), a Wide Area Network (WAN), a mobile wired or wireless network, a private network, a virtual private network, or some combination thereof. Entities in the network 140 exchange data using wired or wireless data links according to various communication protocols.

Figure 2:
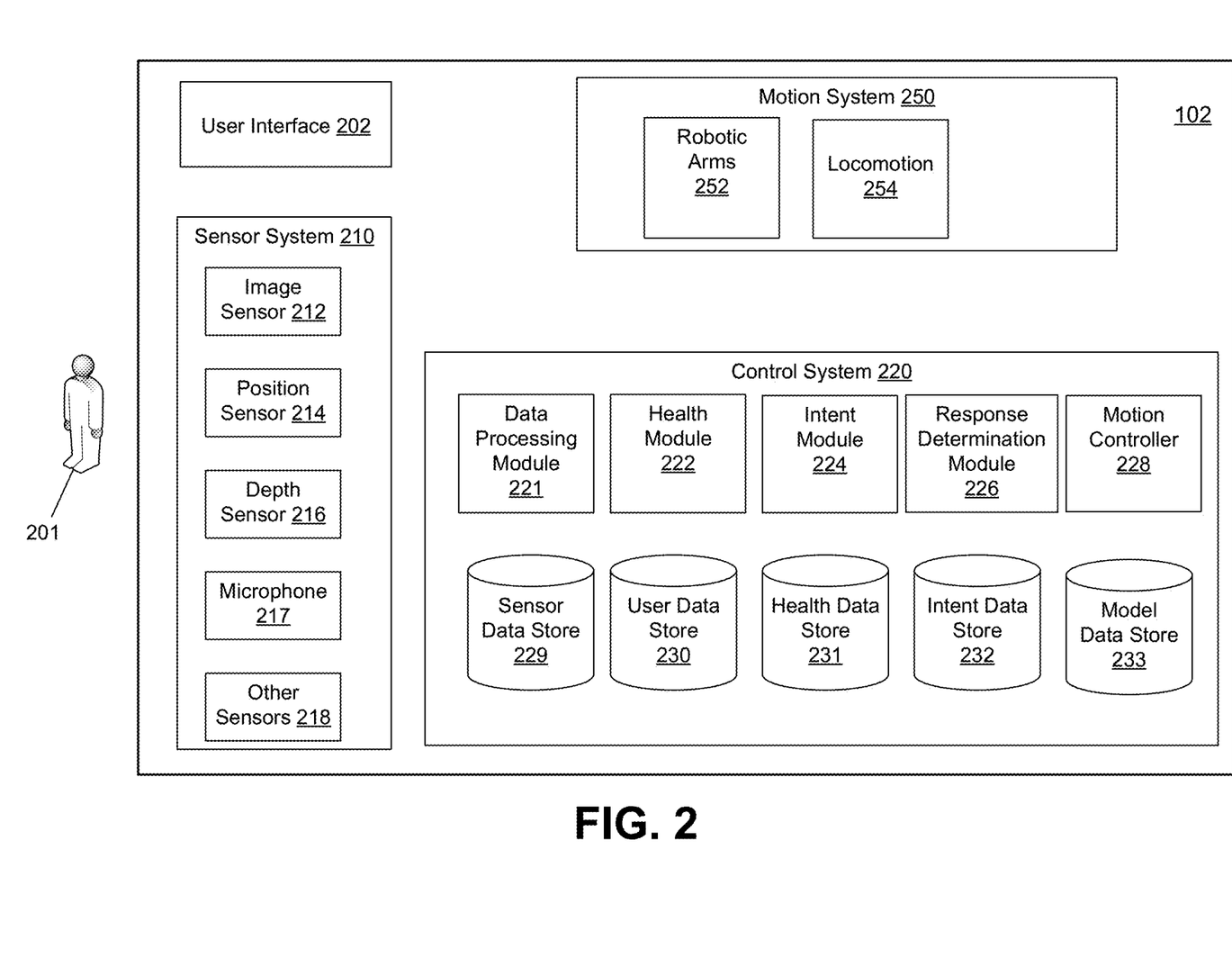
FIG. 2 is a diagram of an assistant robot, according to one embodiment.

FIG. 2 is a diagram of an assistant robot 102, according to one embodiment. The assistant robot 102 is also hereinafter referred to as the robot 102. The robot 102 includes a user interface 202, a sensor system 210, a control system 220, and a motion system 250. In other embodiments, the assistant robot 102 may include additional, fewer, or different components for various applications, which are not shown for purposes of clarity. For example, the assistant robot 102 includes an interface that interfaces with the network 140. The assistant robot 102 may include a communication module, via which another user who may be remote from the assistant robot 102 and user 201 can monitor and control the assistant robot 102. The other user may control the assistant robot's 102 motion, manipulation, and other physical movements. The other user may communicate with the user 201 through the assistant robot 102 via video, audio, and other communication modalities. The other user may control the assistant robot 102 thereby to access other devices such as home devices and health devices.

The user interface 202 interfaces with a user 201. The user interface 202 receives user commands and presents information such as further inquiries, responses, recommended actions, etc. In some embodiments, the user interface 202 includes a voice user interface that permits the user 201 to interact with the assistant robot 102 verbally. The user interface 202 receives voice inputs from the sensor system 210 (e.g., a sound sensor 216) and processes the voice inputs to recognize a command or a request included in the voice inputs. The user interface 202 synthesizes information into speech and outputs the speech to the user 201. The user interface 202 may also include a graphic user interface that receives inputs from I/O devices (e.g., a keyboard, a mouse, a touch pad) or from the client device 110 and provides articulated graphical output on a display. The user interface 202 may include a gesture user interface that receives gesture inputs from the sensor system 210 (e.g., an image sensor 212) and processes the gesture inputs to recognize a command or a request in the gesture inputs. The user interface 202 may include other types of user interfaces.

The sensor system 210 includes sensors that collectively generate data about the user, the surrounding environment of the robot 210, as well as the robot 102. The sensor system 210 includes an image sensor 212 that captures images of the user 201. The images can be two dimensional (2D) or three-dimensional (3D) images. The images can be monochrome or multi-color. The images can be generated by visible light of which the wavelengths are in the range of 400-700 nm or invisible light of which is wavelengths are outside the 400-700 nm range. The sensor system 210 includes a position sensor 214 that measures a position and/or motion of the robot 210. Example position sensors 214 include an accelerometer that measures translational motion (forward/back, up/down, left/right), a gyroscope that measures rotational motion (e.g., pitch, yaw, roll), a magnetometer that measures the earth's magnetic field at the robot's 102 location, a geographical location sensor that measures a location of the robot's 102, or another suitable type of sensor that detects motion. The position sensor 214 may be a part of an inertial measurement unit (IMU) that measures one or more of force, angular rate, and magnetic field surrounding the robot 102. The IMU determines position data of the robot 102 based on measurements generated by the position sensor 214 and/or the depth information generated by the depth sensor 216.

The sensor system 210 includes a depth sensor 216 that measures depth information of objects such as the user 201 in the surrounding environment. The depth information includes the distance and relative location. The depth sensor 216 may be an ultrasonic sensor that captures ultrasound images, a time-of-flight (ToF) camera, or a Lidar. The sensor system 210 includes a microphone 217 that captures sound waves in the surrounding environment.

The sensor system 210 may include other sensors 218. The other sensors 218 may include a pressure sensor to sense an amount of pressure exerted by the robot 102, a touch sensor to detect the contact between the robot 102 and another object such as the user 201, an array microphone to capture sound and source direction in the surrounding environment, a barometer to capture atmospheric pressure in the surrounding environment, and a thermometer to measure an ambient temperature of the surrounding environment or a temperature of another object such as the user 201. The other sensors 218 may further include a hygrometer that measures the humidity in the surrounding environment, and a gas detector that measures a gas concentration in the surrounding environment. The other sensors 218 may include electrodes that measure physiological data of the user 201 such as electromyography (EMG) signals also referred to as muscle data, electrocardiograph (ECG) signals also referred to as heart rate data, electroencephalograph (EEG) signals, magnetoencephalograph (MEG) signals, among other types of signals. The other sensors 216 may include other types of sensors.

The sensors of the sensor system 210 may be integrated in the housing that encloses the components of the robot 102 or be separate from the physical body of the robot 102. For example, a sensor may be attached to the user 201 or be placed in the environment. The sensor system 210 provides the captured information to the user interface 202 or the control system 220 for further processing.

The control system 220 controls the robot 102. For example, the control system 220 determines actions for the robot 102 to perform. Example actions include following the user 201, monitoring the user's 201 actions, recognizing the user's 201 command and responding to the recognized command, determining the user's 201 health condition and responding to the determined health condition, determining the user's 201 intent and responding to the determined intent. The control system 220 determines the user's 201 health condition by using the sensor data generated by the sensor system 210. The control system 220 determines the user's 201 intent by using the sensor data generated by the sensor system 210. In various embodiments, the control system 220 aggregates and analyzes the sensor data from the sensors.

As illustrated, the control system 220 includes a data processing module 221, a health module 222, an intent module 224, a response determination module 226, a motion controller 228, a sensor data store 229, a user data store 230, a health data store 231, an intent data store 232, and a model data store 233. Some embodiments of the control system 220 have different modules than those described here. Similarly, the functions can be distributed among the modules in a different manner that is described here.

The data processing module 221 processes raw sensor data stored in the sensor data store 229. For example, the data processing module 222 may process images to recognize an action (e.g., walking, sitting, holding an object, opening a door, petting a dog, reaching for an object, etc.), a gesture (e.g., right hand wave, left hand wave, head nod, twist arm, etc.), a body part (e.g., a face, a hand, an arm etc.) a facial expression (e.g., smile, frown, cry, surprised, agitated, etc.), a body position (e.g., standing on both legs, standing on left leg, standing on right leg, supine, prone, right lateral recumbent, left lateral recumbent, etc.), a physical appearance (e.g., a skin condition such as rash, a droopy face, a piece of clothing, etc.), an object (e.g., a cup, a dog, a cat, a suitcase, a key, etc.) The health module 222 may process sound signals to recognize spoken content (e.g., a word, a phrase, a request, and the like), a speech characteristic (e.g., a pitch, a volume, a speed, etc.), and the like. As another example, the health module 222 may determine temporal information (e.g., a starting time, an end time, a time duration, etc.) and/or locational information (e.g., a geographic location, a zone in a building (e.g., living room, bedroom, kitchen, bathroom, basement, stairway, office, etc.), a relative position with an object, etc.) of an action, a gesture, a face, a facial expression, spoken content (e.g., a word, a phrase, a request, and the like), a speech characteristic (e.g., a pitch, a volume, a speed, etc.), and the like. As a further example, the health module 222 determines a temporal characteristic (e.g., a rate during a time interval, a time period, etc.) of a particular action, gesture, facial expression, spoken content, and the like. The time interval and the time period may be configured by the user 201 or by an administrator according to a recommended guideline. The time interval and the time period may be varied.

The data processing module 221 may determine a routine of the user 201 such as the user's 201 typical sleeping hours and other habits, and a daily time distribution of the user's 201 location. The data processing module 221 may employ one or more data processing algorithms, classifiers, artificial intelligence models, machine learning models stored in the model data store 237 to process the sensor data as described above.

The health module 222 determines the user's 201 health condition. The health condition includes a likelihood of the user 201 being healthy, unhealthy, injured, or subject to a health threat. The health module 222 may further diagnose a type of medical condition. Example medical conditions include fever, breath shortness, digestive problems, dehydration, stroke, and the like. The health module 222 determines the health condition using the raw sensor data generated by the sensor system 210 and/or processed data output by the data processing module 221. The health condition may be additionally determined by the user data stored in the user data store 230.

The health module 222 can detect that the user 201 may have a potential health problem based on the sensor data indicating that the user 201 acts irregularly. That is, if the user's 201 behavior deviates from the normal behavior. The normal behavior can be general normal behavior determined from data about the general population or specific normal behavior determined from data about the user's 201 historical behavior. The health module 222 may further diagnose the user's 201 specific health condition by comparing the user's 201 behavior to categorized known conditions. For example, if the sensor data indicates that the user is asleep (or unconscious) in a new and unusual location (e.g., hallway) and the user 201 normally sleeps in one location (e.g., in the bedroom), the health module 222 determines that the user 201 may have fainted. If the sensor data indicates that the user opens windows too often, the health module 222 determines that the user 201 may have a shortness of breath. If the sensor data indicates that the user 201 goes to the bathroom more often than usual, the health module 222 determines that the user 201 may have digestive problems or kidney disease. If the sensor data indicates that the user 201 is asleep (or unconscious) longer than usual, the health module 222 determines that the user 201 may have a fever, inflammation, anemia, hypothyroidism, or heart disease. If the sensor data indicates that the user 201 has a higher than normal body temperature, the health module 222 determines that the user 201 may have a fever or inflammation. If the sensor data indicates that the user 201 coughs, the health module 222 determines that the user 201 may have caught a cold. If the sensor data indicates that the user 201 wanders around at night during sleeping hours, the health module 222 determines that the user 201 may be sleepwalking. If the sensor data indicates that the user 201 sets the air conditioner temperature to a higher than normal temperature regularly, the health module 222 determines that the user 201 may have problems with the blood circulatory system. If the sensor data indicates that the user 201 forgets about activities typically performed, the health module 222 determines that the user 201 may have dementia. If the sensor data indicates that the user 201 blows the nose, the health module 222 determines that the user 201 may have caught a cold or an allergy.

The health module 222 can detect that the user 201 may be injured based on the sensor data indicating that the user 201 acts unexpectedly. The health module 222 may further diagnose the user's 201 specific health condition by comparing the user's 201 behavior to categorized known conditions. If the sensor data indicates that the user 201 screams and falls down, the health module 222 determines that the user 201 may have suffered an ankle sprain or head injury. If the sensor data indicates that the user 201 has a shortness of breath and notices that the person faints, the health module 222 determines that the user 201 may have suffered a heart rhythm disorder. If the sensor data indicates that the user 201 has a change in speech habits or face asymmetry, the health module 222 determines that the user 201 may have suffered a stroke. If the sensor data indicates that the user 201 has jaundice, the health module 222 determines that the user 201 may have a kidney disease or hepatitis.

The health module 222 can detect that the user 201 may be at a health risk based on the sensor data indicating that the environment is unsafe. If the sensor data indicates that carbon monoxide is building up or there is rot or mold, the health module 222 determines that the environment is not safe for the user 201.

The health module 222 may provide the sensor data to one or more machine learning models to determine the health condition. The machine learning models include one or more artificial intelligence models, classifiers (e.g., logistic classifiers, support vector machines, and multi-class classification), decision trees, neural networks, deep learning models, or any combination thereof. The machine learning models include correlations between the health condition and sensor data. The sensor data include physical condition features, mental condition features, behavior features, environment features, and the like. In some embodiments, the machine learning models include correlations between one or more features included in the sensor data and the health condition. For example, model parameters of a logistic classifier include the coefficients of the logistic function that correspond to different features included in the sensor data.

As another example, the machine learning models include a decision tree model, which is a directed acyclic graph where nodes correspond to conditional tests for a feature included in the sensor data and leaves correspond to classification outcomes (i.e., presence or absence of one or more features). The parameters of the example decision tree include (1) an adjacency matrix describing the connections between nodes and leaves of the decision tree; (2) node parameters indicating a compared feature, a comparison threshold, and a type of comparison (e.g., greater than, equal to, less than) for a node; and/or (3) leaf parameters indicating which health condition correspond to which leaves of the decision tree.

The health module 222 creates machine learning models (e.g., determines the model parameters) by using training data. The training data includes a set of raw or analyzed sensor data labeled with features. For example, the training data are sensor data for which features have already been identified (e.g., by the health module 222, by the user 201, by an administrator, by an expert, or a combination thereof). The health module 222 determines the model parameters that predict the health conditions associated with the sensor data. For example, the health module 222 determines an objective function indicating the degree to which the determined health conditions matching the health conditions indicated in the training data. The health module 222 modifies the parameters to optimize the objective function, thereby reducing differences between predicted health conditions and actual health conditions.

Figure 4:
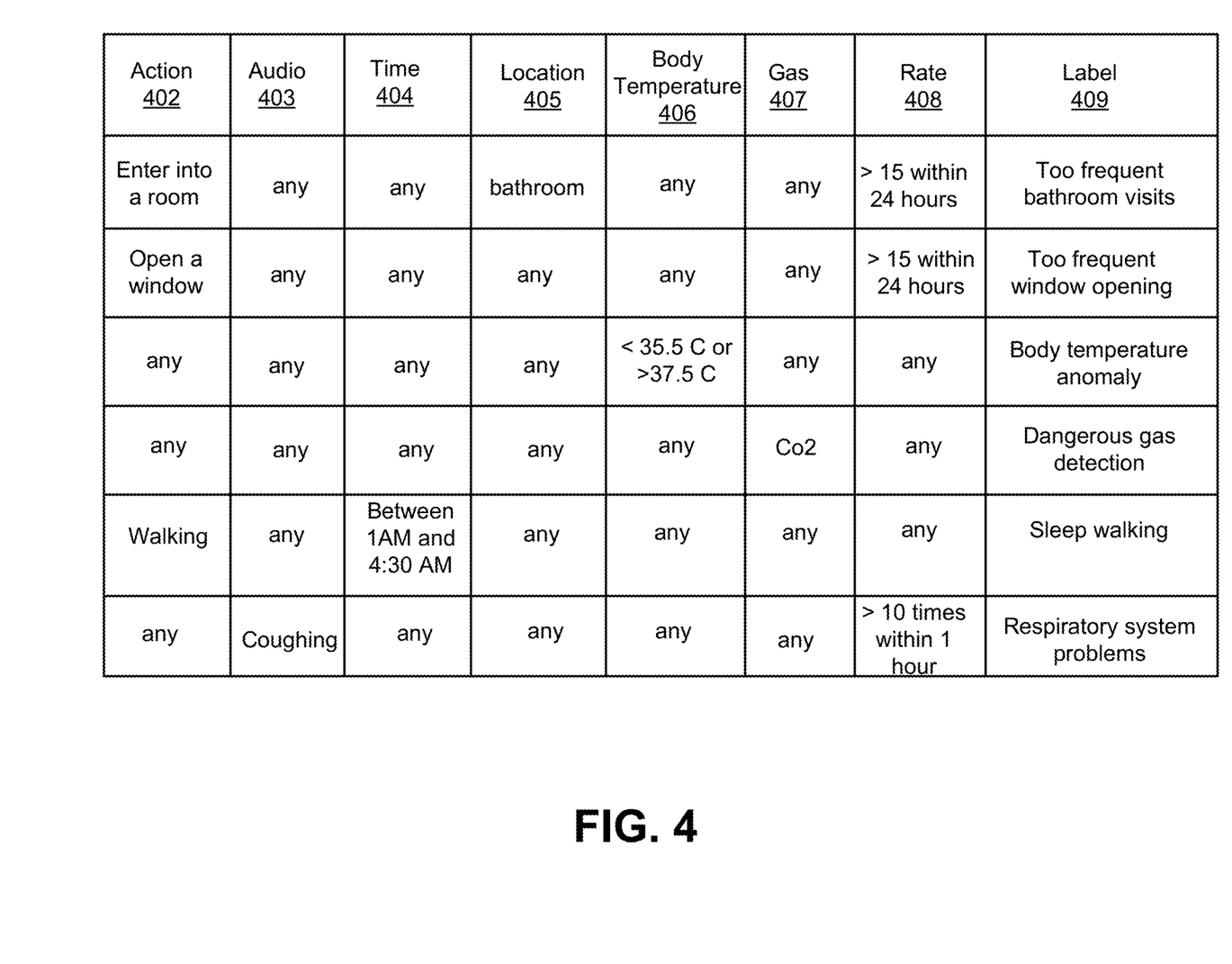
FIG. 4 is a table illustrating training data, according to one embodiment.

One example of labeled training data is illustrated in FIG. 4. Data is organized in a table format where each row is a record of data and the associated label. The columns 402 through 408 are different types of data and the column 409 is the labels. The labels may be created according to publicly available information or personalized information. Example publicly available research results include the normal body temperature range, the normal heart beat range, the normal blood pressure range, the normal weight range for individuals having similar demographic information such as age, ethnicity, and gender. Example personalized information includes the user's habits or schedules such as regular sleep hours, weight history, and the like. Some training data is constructed during the first few days the robot 102 interacts with the user 201 and can be continuously/periodically updated, e.g., usual sleeping hours and other habits. The robot 102 may create a daily time distribution of the user's 201 normal location for activities. For example, the user 201 stays in the kitchen during 6-8 AM and 6-8 PM on weekdays, in the living room 8-10 PM on weekdays, in the bedroom 10 PM-6 AM on weekdays.

The health module 222 further updates machine learning models (e.g., model parameters of the machine learning models) using information received, for example, via the user interface 202 and/or the sensor system 210. For example, after the robot 102 determines a health condition based on the sensor data, the robot 102 confirms with the user 201 on the health condition. The user's 201 positive feedback (e.g., confirmation) indicates that the machine learning models are accurate and negative feedback (e.g., disapproval) indicates that the machine learning models need to be improved.

The intent module 224 determines the user's intent. The intent described herein includes the user's intention or plan to complete a task, need for a task to be complete, or a regularly-performed task that should be complete. The intent module 224 determines the intent using the raw sensor data generated by the sensor system 210 and/or processed data output by the data processing module 221. The intent may be determined by further using the user data stored in the user data store 230 and/or querying the internet.

The intent module 224 can determine the user's intent by recognizing a current activity that the user 201 is undertaking, the user's 201 routine, and contextual information. As one example, the intent module 224 determines that the user 201 intends to perform an action on an object (e.g., have a water bottle, pick up a box, carry a dish, etc.) if the user 201 points at an object. The intent module 224 determines that the user is likely to have a coffee and take a shower if the user 201 is waking up in the morning. The intent module 224 determines that the user 201 is getting ready for bed and will intend to lock doors if the user 201 starts to brush teeth at night. The intent module 224 determines that the user 201 is going to work and will need the laptop if the user 201 has had breakfast and is putting on work clothes. The intent module 224 determines that the user is likely to be home soon and turns on the air conditioner if the time is approaching the user's regular home hours.

The intent module 224 determines that the user 201 is starting to cook dinner and may likely need a recipe if the user 201 is taking out ingredients from the fridge after work. The intent module 224 determines that the user 201 is working and may need coffee if the user 201 is yawning in front of the computer. The intent module 224 determines that the user 201 is about to watch TV and will likely need program recommendation or snacks if the user 201 turns on the TV. The intent module 224 determines that the house will be vacant and the user 201 will need to turn off house appliances if the user 201 is the last person to leave the house. The intent module 224 determines that the user 201 is going out if the user 201 is putting on shoes in one room and grabbing keys in another room. The intent module 224 determines that the user 201 may likely need an umbrella if the sensor data indicates that it will rain. The intent module 224 determines that the user 201 will likely restock a particular food or house supplies if the sensor data indicates that the food or house supplies have a low stock. The intent module 224 determines that the user 201 may be interested in knowing promotions on items that the user 201 regularly orders if there are promotions.

In addition, the intent module 224 determines that the pet is hungry and needs to be fed if the pet regular feeding schedule has been missed. The intent module 224 determines that the user 201 is likely to water a plant if the user 201 waters the plant every week. The intent module 224 determines that the user 201 may need to do house cleaning if the sensor data indicates that clothes are scattered around the house/apartment. The intent module 224 determines that the user 201 may need to do the laundry if the sensor data indicates that the laundry basket is full. The intent module 224 determines that the user 201 may need to do the dishes if the sensor data indicates that the dishwasher is full or nearly full. The intent module 224 determines that the air conditioner needs to be adjusted if the person is sweating or is rubbing hands with hunched shoulders. The intent module 224 determines that a particular food may cause allergy to the user 201 if the sensor data indicates that the food includes an allergen.

The intent module 222 may provide the sensor data to one or more machine learning models to determine the intent. The machine learning models include one or more artificial intelligence models, classifiers (e.g., logistic classifiers, support vector machines, and multi-class classification), decision trees, neural networks, deep learning models, or any combination thereof. The machine learning models include correlations between the intent and sensor data. The sensor data includes activity features, schedule features, behavior features, environment features, and the like. In some embodiments, the machine learning models include correlations between one or more features included in the sensor data and the intent. For example, model parameters of a logistic classifier include the coefficients of the logistic function that correspond to different features included in the sensor data.

As another example, the machine learning models include a decision tree model, which is a directed acyclic graph where nodes correspond to conditional tests for a feature included in the sensor data and leaves correspond to classification outcomes (i.e., presence or absence of one or more features). The parameters of the example decision tree include (1) an adjacency matrix describing the connections between nodes and leaves of the decision tree; (2) node parameters indicating a compared feature, a comparison threshold, and a type of comparison (e.g., greater than, equal to, less than) for a node; and/or (3) leaf parameters indicating which intent corresponds to which leaves of the decision tree.

The intent module 224 creates machine learning models (e.g., determines the model parameters) by using training data. The training data includes a set of raw or analyzed sensor data labeled with features. For example, the training data are sensor data for which features have already been identified (e.g., by the health module 224, by the user 201, by an administrator, by an expert, or a combination thereof). The intent module 224 determines the model parameters that predict the intent associated with the sensor data. For example, the intent module 222 determines an objective function indicating the degree to which the determined intent matching the intent indicated in the training data. The health module 222 modifies the parameters to optimize the objective function, thereby reducing differences between predicted intent and actual intent.

Figure 6:
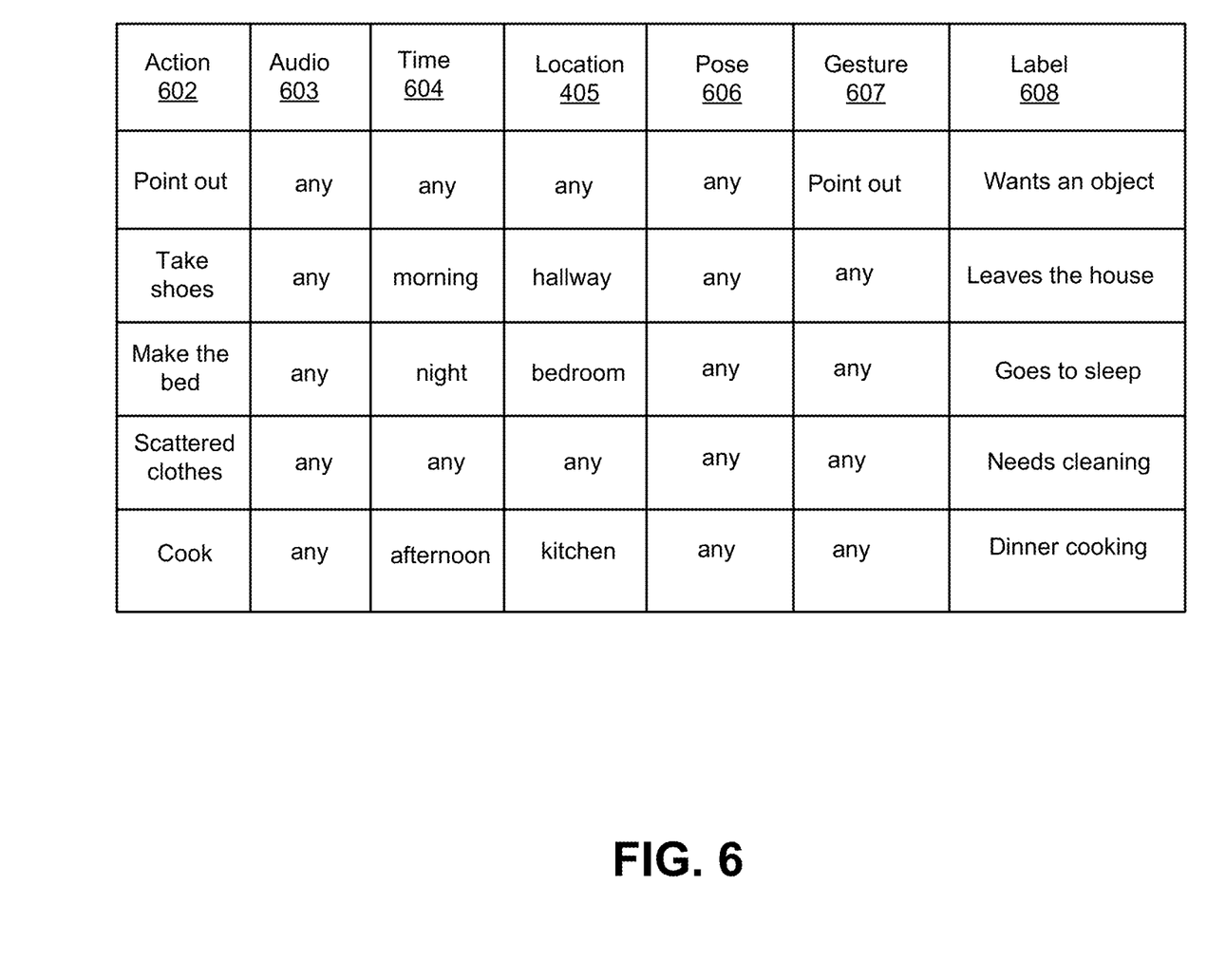
FIG. 6 is a table illustrating training data, according to one embodiment.

One example of labeled training data is illustrated in FIG. 6. Data is organized in a table format where each row is a record of data and the associated label. The columns 602 through 608 are different types of data and the column 608 is the labels. The labels may be created according to publicly available information or personalized information. Example publicly available research results include humans' typical behavior in a situation. Example personalized information includes the user's habits or schedules such as regular sleep hours, work hours, location schedules, and the like. Some training data is constructed during the first few days the robot 102 interacts with the user 201 and can be continuously/periodically updated, e.g., usual sleeping hours and other habits. The robot 102 may create a daily time distribution of the user's 201 normal location for activities. For example, the user 201 stays in the kitchen during 6-8 AM and 6-8 PM on weekdays, in the living room 8-10 PM on weekdays, in the bedroom 10 PM-6 AM on weekdays.

The intent module 224 further updates machine learning models (e.g., model parameters of the machine learning models) using information received, for example, via the user interface 202. For example, after the robot 102 determines an intent based on the sensor data, the robot 102 confirms with the user 201 on the intent. The user's 201 positive feedback (e.g., confirmation) indicates that the machine learning models are accurate and negative feedback (e.g., disapproval) indicates that the machine learning models need to be improved.

The response determination module 226 determines the robot's 102 response based on the user's health condition or based on the user's intent. For example, if the health module 222 determines that the user 201 may have a potential health problem, the response determination module 226 determines to confirm with the user 201 on whether the user 201 needs assistance and/or to offer assistance. If the user 201 affirms, the response determination module 226 determines to contact another party (e.g., a physician, an emergency contact, another user nearby, etc.) and/or to provide assistance. For example, the response determination module 226 determines to ask the user 201 for additional input thereby to diagnose the user 201, and/or fetch medicine, water, tissue, or other supplies. The response determination module 226 approaches another individual nearby to communicate and/or calls another individual via telephone or text. If the health module 222 determines that the user 201 is injured, the response determination module 226 determines to confirm with the user 201 whether an emergency call should be placed and/or to contact places an emergency call. If the health module 222 determines that the user 201 faces a health risk, the response determination module 226 alerts the user 201 about the health risk (e.g., carbon monoxide, mold, etc.) and asks for further instructions.

The response determination module 226 may further associate information such as the user 201's confirmation, instructions, and diagnosis with the sensor data and store the information in the user data store 230 and the health data store 232. The control system 220 may provide log daily observations of health state for later analysis by the robot or medical professionals.

The response determination module 226 may determine to complete the task to further the determined intent and/or to confirm with the user to receive further instructions. For example, if the intent module 224 determines that the user

201 intends to perform an action on an object (e.g., have a water bottle, pick up a box, carry a dish, etc.), the response determination module 226 determines to perform the action. If the intent module 224 determines that the user is performing a routine (e.g., waking up, goes to bed, goes to work, arrives at home, cooking dinner, watching tv, working, etc.), the response determination module 226 determines to offer assistance or to provide the assistance (e.g., making the coffee, locking all doors, turning on or off home devices, bringing the laptop, providing recipes, recommending tv programs, bringing snacks, etc.) If the intent module 224 determines that the schedule is due (e.g., feeding schedule, watering schedule, ordering schedule, laundry schedule, etc.), the response determination module 226 determines to offer assistance or to provide the assistance (e.g., feed the pet, water the plant, order pantry items or house supplies, etc.) If the intent module determines that the user will likely need a particular object (e.g., an umbrella, a promotion, a new release, etc.) or perform a task (e.g., do the laundry, do the dishes, adjust the air conditioner), the response determination module 226 determines to offer assistance or to provide the assistance (e.g., bring the umbrella, notifies the promotion, notifies the new release, put the clothes in the laundry basket or in the washing machine, load the washing machine, load the dishes, start or unload the dish washer, etc.)

The control system 220 controls the robot 102 to react based on the response determined by the response determination module 226. The motion controller 226 determines a set of motions for the motion system 250 to perform based on the response determined by the control system 220. For example, if the response determination module 226 determines to go to a specification location, the motion controller 228 generates instructions to drive the locomotion system 254 (e.g., wheels, legs, treads, etc.) toward the location of the user 201. If the response determination module 226 determines to perform an action, the motion controller generates instructions to drive the robotic arms 252 to perform the action. The control system 220 may also communicate with the device 106 or the client device 110 to turn on or off a device, to send an alert to the user 201 via the client device 110, or to send an alert to another party.

The user data store 230 stores data about the user 201. The user data includes the user's personal information (e.g., age, height, weight, gender, face, etc.), health information (e.g., medical history, health records, allergy, etc.), behavior information (e.g., walking speed, speech speed, poses, routines, habits, a distribution of location, etc.), contact information (e.g., contact number, email address, home address, etc.), preferences (e.g., food, movies, books, hobbies etc.), wardrobe (e.g., casual clothing, work clothing, business clothing, special occasion, etc.) and the like.

The health data store 231 stores health condition data such as information describing illness and associated symptoms, information describing human behavior and associated medical conditions, information describing injury and associated human behaviors, information describing mental illness and physical manifestations, and the like. The intent data store 232 stores intent data such as information describing human behavior and associated tasks, information describing human behavior and associated objectives, information describing an environment and associated common human reaction in the environment, information describing a context and associated common human reaction in the context, and the like. The model data store 233 stores the machine learning models used by the robot 102. The machine learning models 102 may be trained by the robot 102. The machine learning models 102 may be additionally trained by the assistant platform 120 and deployed to the robot 102.

Figure 3:
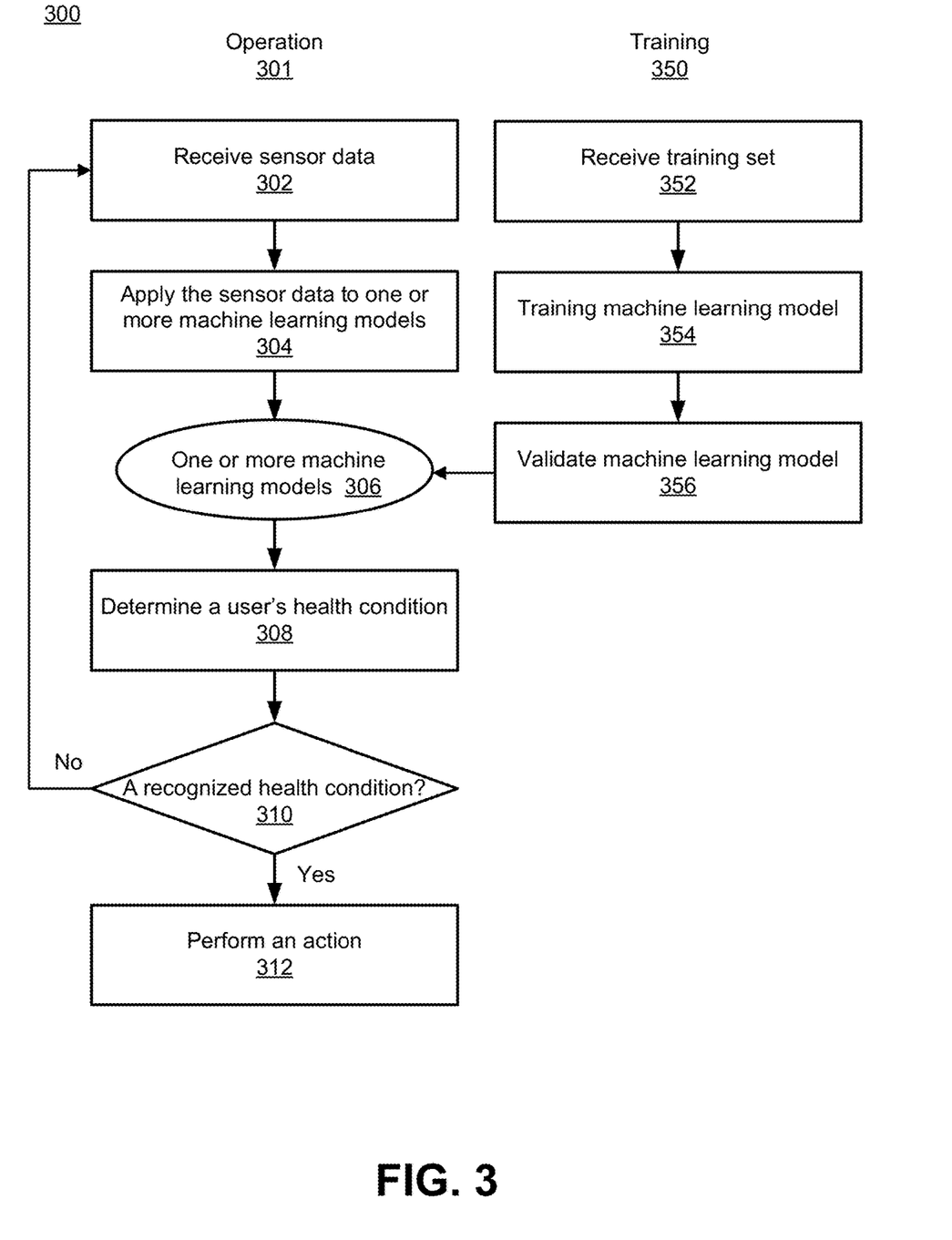
FIG. 3 is a flow chart illustrating the control system determining a user's health condition, according to one embodiment.

The motion system 250 includes physical components that carry out actions. For example, the robotic arms 252 can perform operations toward an object or a human. Example operations include touch, grasp, hold, move, release, wave, shake, lift, drop, place, turn, twist, and the like. The robotic arms 252 can have various ranges of motion. The locomotion system 254 can perform operations thereby to move the robot assistant 102 to a destination. The motion system 250 may include other components such as actuators, motors, FIG. 3 is a flow chart illustrating the control system 220 determining a user's health condition, according to one embodiment. The process 300 includes an operation phase 301 where the control system 220 uses trained machine learning models and a training phase 350 where the control system 220 trains the machine learning models. The control system 220 receives 302 sensor data from the sensor system 210. The control system 220 applies 304 the sensor data to one or more machine learning models 306. The control system may process the sensor data before providing the sensor data to the machine learning models. The control system may provide only a portion of the sensor data to the machine learning models. The control system 220 determines 308 the user health condition using the output of the one or more machine learning models 306. The control system 220 determines 310 whether the health condition is a recognized health condition. If the health condition is one of the recognized conditions, the control system 220 performs 312 an action. If the health condition is not one of the recognized conditions, the control system 220 may search the internet, or confirm with the user for further information, or contact a medical professional.

On the training side, the control system 220 receives 352 one or more training sets including data labeled. The control system 220 provides 354 the training sets to one or more machine learning models for the machine learning models to determine the correlations between sensor data and health conditions. The control system 220 validates the trained machine learning models before using the machine learning models. For example, the control system 220 applies validation data sets of the trained machine learning models until the trained machine learning models' output is accurate. The control system 220 may train the machine learning models while operating the machine learning models.

Figure 5:
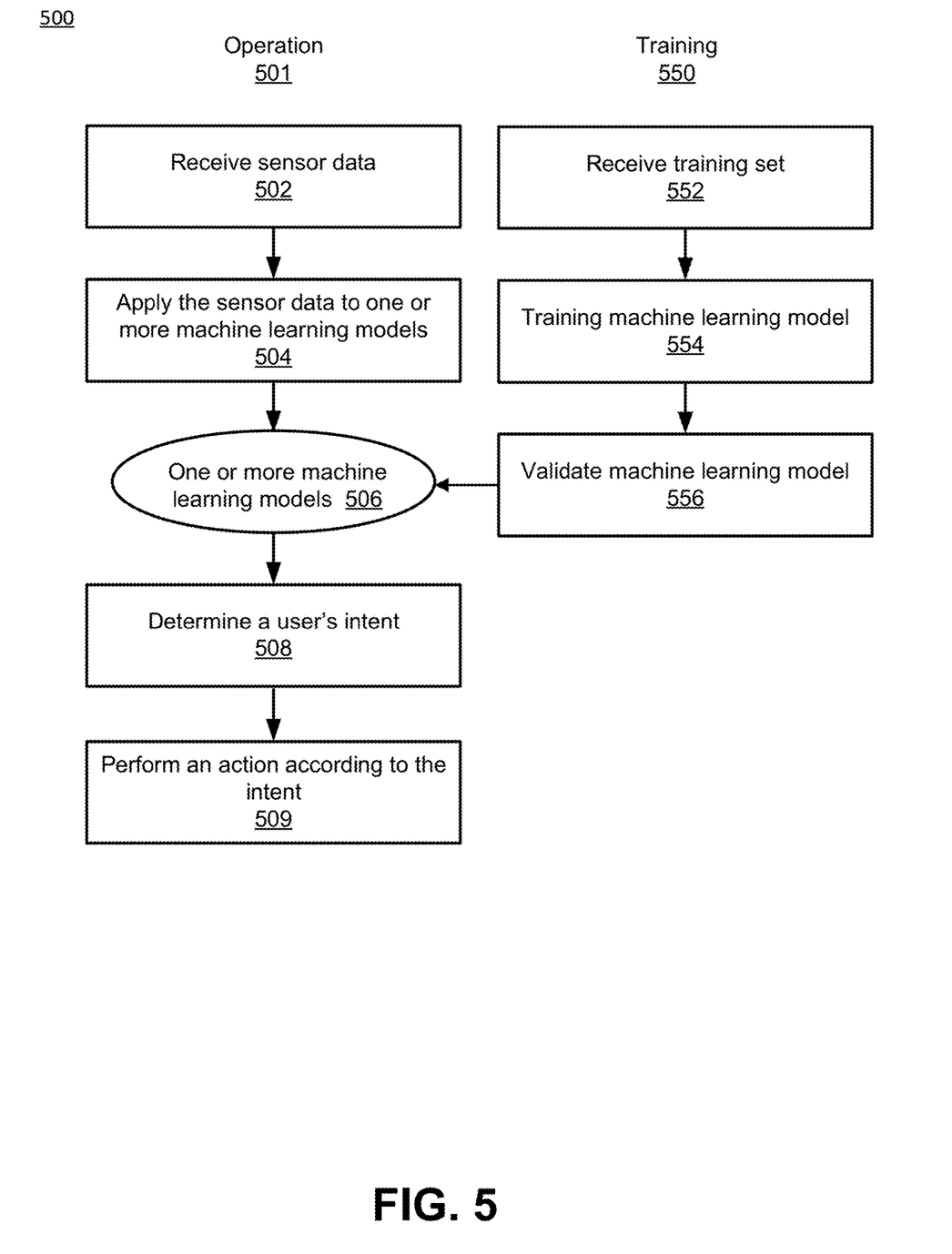
FIG. 5 is a flow chart illustrating the control system determining a user's intent, according to one embodiment.

FIG. 5 is a flow chart illustrating the control system 220 determining a user's intent, according to one embodiment. The process 500 includes an operation phase 501 where the control system 220 uses trained machine learning models and a training phase 550 where the control system 220 trains the machine learning models. The control system 220 receives 502 sensor data from the sensor system 210. The control system 220 applies 504 the sensor data to one or more machine learning models 506. The control system may process the sensor data before providing the sensor data to the machine learning models. The control system may provide only a portion of the sensor data to the machine learning models. The control system 220 determines 508 the user intent using the output of the one or more machine learning models 506. The control system 220 performs 312 an action according to the intent.

On the training side, the control system 220 receives 552 one or more training sets including data labeled. The control system 220 provides 554 the training sets to one or more machine learning models for the machine learning models to determine the correlations between sensor data and intent.

The control system 220 validates 556 the trained machine learning models before using the machine learning models. For example, the control system 220 applies validation data sets of the trained machine learning models until the trained machine learning models' output is accurate. The control system 220 may train the machine learning models while operating the machine learning models.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A robotic device, comprising:
   a plurality of sensors configured to:
      capture a set of one or more images of an individual,
      record sound signals of the individual, and
      generate environment data of an environment surrounding the individual;
   a processor; and
   memory storing instructions configured to cause the processor to perform:
      recognizing a set of actions performed by the individual from the set of one or more images of the individual;
      recognizing verbal content from the individual from the sound signals;
      inputting the set of actions performed by the individual, past actions of the individual, the verbal content from the individual, and the environment data to a machine learning model to predict the individual's intent, wherein training of the machine learning model comprises:
         initiating the machine learning model with a set of parameters and an objective function, the set of parameters comprising a first set of parameters related to sensor data captured by the plurality of sensors, a second set of parameters related to individual's schedules, a third set of parameters related to typical human behaviors;
         generating a first set of training data related to past observed situations, the first set of training data comprising the past actions of the individual, sensor data captured by the plurality of sensors capturing during the past observed situations, and labels of identified intents corresponding to the past observed situations;
         capturing individual's schedules, the individual's schedules comprising time and locations of past individual actions;
         generating a second set of training data related to one or more daily time distributions of the individual's schedules;
         generating a third set of training data related to publicly available information of human typical behavior in one or more situations;
         inputting the first set of training data related to past observed situations, the second set of training data related to one or more daily time distributions of the individual's schedules, the third set of training data related to publicly available information of human typical behavior to the machine learning model for the machine learning model to determine predicted intents of the past observed situations;
         determining a value of the objective function that measures a degree of matching between the predicted intents of the past observed situations and the labels of identified intents recorded in the past observed situations; and
      adjusting the first set of parameters related to sensor data captured by the plurality of sensors, the second set of parameters related to individual's schedules, the third set of parameters related to typical human behaviors of the machine learning model based on the value of the objective function;
      identifying one or more tasks corresponding to the individual's intent; and
      determining a set of actions to be performed by the robotic device based on the one or more tasks.

2. The robotic device of claim 1, wherein the instructions further cause the processor to perform: determining whether the set of actions performed by the individual is included in a plurality of predetermined actions, a predetermined action corresponding to a predetermined intent.

3. The robotic device of claim 1, wherein the instructions further cause the processor to perform: determining whether the verbal content is included in a plurality of predetermined verbal content, a predetermined verbal content corresponding to a predetermined intent.

4. The robotic device of claim 1, wherein the instructions further cause the processor to perform: determining a temporal characteristic of each of the set of actions, and wherein the intent is determined based at least on the temporal characteristic.

5. The robotic device of claim 1, wherein the environment data includes at least one of an ambient temperature, a time, a location, an object, and a location of the object relative to the individual.

6. The robotic device of claim 1, wherein the instructions further cause the processor to perform:
responsive to determining the set of actions performed by the individual is similar to a behavior schedule, determining that the intent based on a behavior routine.

7. The robotic device of claim 6, wherein the instructions further cause the processor to perform: determining the behavior schedule from historical actions of the individual, the verbal content of the individual, and the environment data.

8. The robotic device of claim 1, wherein the set of actions performed by the robotic device includes one or more of the following: following the individual, alerting the individual, monitoring the individual, assisting the individual, or sending an alert to another user.

9. The robotic device of claim 1, wherein the one or more tasks includes one or more of the following: fetching an object, turning on a device, turning off a device, querying the internet, or providing information.

10. The robotic device of claim 1, wherein the set of actions performed by the robotic device includes:
providing the one or more tasks to the individual;
receiving a confirmation from the individual; and
updating the machine learning model based on the confirmation from the individual.

11. The robotic device of claim 9, further comprising at least a robotic arm and a locomotion system.

12. The robotic device of claim 9, wherein the sensors comprise one or more of: a camera, a microphone, a position sensor, a depth sensor, a pressure sensor, a touch sensor, a barometer, a thermometer, a hygrometer, or a gas detector.

13. A method, comprising:
capturing, by a robotic device, a set of one or more images of an individual;
recording, by the robotic device, sound signals of the individual,
generating, by the robotic device, environment data of an environment surrounding the individual;
recognizing, by the robotic device, a set of actions performed by the individual from the set of one or more images of the individual;
recognizing, by the robotic device, verbal content from the individual from the sound signals;
inputting the set of actions performed by the individual, past actions of the individual, the verbal content from the individual, and the environment data to a machine learning model to predict the individual's intent, wherein training of the machine learning model comprises:
initiating the machine learning model with a set of parameters and an objective function, the set of parameters comprising a first set of parameters related to sensor data captured by a plurality of sensors, a second set of parameters related to individual's schedules, a third set of parameters related to typical human behaviors;
generating a first set of training data related to past observed situations, the first set of training data comprising the past actions of the individual, sensor data captured by the plurality of sensors capturing during the past observed situations, and labels of identified intents corresponding to the past observed situations;
capturing individual's schedules, the individual's schedules comprising time and locations of past individual actions;
generating a second set of training data related to one or more daily time distributions of the individual's schedules;
generating a third set of training data related to publicly available information of human typical behavior in one or more situations;
inputting the first set of training data related to past observed situations, the second set of training data related to one or more daily time distributions of the individual's schedules, the third set of training data related to publicly available information of human typical behavior to the machine learning model for the machine learning model to determine predicted intents of the past observed situations;
determining a value of the objective function that measures a degree of matching between the predicted intents of the past observed situations and the labels of identified intents recorded in the past observed situations; and
adjusting the first set of parameters related to sensor data captured by the plurality of sensors, the second set of parameters related to individual's schedules, the third set of parameters related to typical human behaviors of the machine learning model based on the value of the objective function;
identifying, by the robotic device, one or more tasks corresponding to the individual's intent; and
determining, by the robotic device, a set of actions to be performed by the robotic device based on the one or more tasks.

14. The method of claim 13, further comprising determining whether the verbal content is included in a plurality of predetermined verbal content, a predetermined verbal content corresponding to a predetermined intent.

15. The method of claim 13, further comprising:
responsive to determining the set of actions performed by the individual is similar to a behavior schedule, determining that the intent based on a behavior routine.

16. The method of claim 15, further comprising determining the behavior schedule from historical actions of the individual, the verbal content of the individual, and the environment data.

17. The method of claim 13, wherein the set of actions to be performed by the robotic device includes:
providing the one or more tasks to the individual;
receiving a confirmation from the individual; and
updating the machine learning model based on the confirmation from the individual.

18. The method of claim 13, wherein the one or more tasks includes one or more of the following: fetching an object, turning on a device, turning off a device, querying the internet, or providing information.

19. The method of claim 13, wherein the robotic device comprises at least a robotic arm and a locomotion system.

20. The method of claim 13, wherein the robotic device comprises a plurality of sensors, the sensors comprise one or more of: a camera, a microphone, a position sensor, a depth sensor, a pressure sensor, a touch sensor, a barometer, a thermometer, a hygrometer, or a gas detector.

* * * * *